US005484405A

United States Patent [19]

Edstrom, Sr.

[11] Patent Number: 5,484,405

[45] Date of Patent: Jan. 16, 1996

[54] DRINKING DEVICE FOR HANDICAPPED PERSONS

[76] Inventor: William E. Edstrom, Sr., 28324 E. Main St., Waterford, Wis. 53185

[21] Appl. No.: 273,896

[22] Filed: Jul. 12, 1994

[51] Int. Cl.[6] .................................................. A61M 31/00

[52] U.S. Cl. .................................................. 604/77; 604/79

[58] Field of Search .............................. 604/77, 281, 282, 604/78–82; 239/33, 36, 37

[56] References Cited

U.S. PATENT DOCUMENTS 591,228 10/1897 Goltermann .
1,431,860 10/1922 Zurbrigg .
1,731,322 10/1927 Riddle .
2,756,740 7/1956 Deane .
2,759,765 8/1956 Pawley .
2,969,064 1/1961 Metz .
3,550,560 12/1970 Edstrom .
3,698,685 10/1972 Lang .
4,258,666 3/1981 Edstrom .
4,391,225 7/1983 Sparks .
4,699,319 10/1987 Green .
4,966,580 10/1990 Turner et al. ......................... 604/79 X
5,057,077 10/1991 Turner et al. .
5,060,833 10/1991 Edison et al. .

FOREIGN PATENT DOCUMENTS 4137132 5/1993 Germany ............................... 604/282

*Primary Examiner*—John D. Yasko

[57] ABSTRACT

A drinking device is sanitary, easy to clean, and heightens the user's level of independence by (1) being readily yet semi-permanently positionable at a location permitting access to the device by the mouth of the user; and (2) being easily activated by the mouth of the user to reliably and continuously supply liquid to the user upon demand using only the user's mouth. The device includes a mouth operated drinking valve the semi-permanent positioning of which for accessibility by the mouth of the user is made possible by a tubing assembly in the form a flexible tube supported by a stiffener. The stiffener permits the tubing assembly to be readily bent to position the tube and drinking valve as desired yet maintains its position after bending. The stiffener is provided on the outside rather than within the flexible tube to facilitate cleaning of the tube and thus to promote sanitary use. Cleaning is further facilitated and sanitary use further promoted through the use of an easily disassembled device including a bottle with a removable lid, an easily disassembled drinking valve, and easily detachable connection of the tubing assembly to the bottle and valve.

15 Claims, 5 Drawing Sheets

DRINKING DEVICE FOR HANDICAPPED PERSONS

BACKGROUND OF THE INVENTION

1. Field of the Invention

The invention relates to drinking devices and, more particularly, relates to drinking devices for quadriplegics, patients recovering from surgery or suffering from a debilitating illness, or other persons having limited or no use of their hands.

2. Description of the Related Art

For people such as quadriplegics, stroke victims, hospital patients recovering from major surgery or suffering from a debilitating illness, or anyone else having limited or no use of their hands, unassisted drinking can be a serious problem. Picking up a water glass and drinking directly from it are out of the question. Drinking out of a straw is also impossible unless an attendant holds the water glass and straw at a location permitting access to the straw by the user's mouth. This of course requires heavy dependence by the user on attendants and thus seriously damps feelings of independence. This also places some users at considerable risk of dehydration if their attendants are unavailable for periods of time exceeding several hours or more. Even assisted drinking from a straw may be impossible for users who are too weak to suck on the straw. A need has therefore been established for a drinking device which permits unassisted access to fluids by even highly incapacitated users.

Several devices have heretofore been proposed to meet this need, but all such devices have exhibited marked drawbacks and disadvantages. For instance, a device is proposed in U.S. Pat. No. 4,699,319 to Green which includes a jug for storing water or another fluid, and a tubing assembly including (1) a rigid tube having an inlet positioned in the jug and an outlet extending above and forwardly from the jug, and (2) a flexible straw extending forwardly from the outlet of the tube for access by the mouth of the user. Only a relatively short portion of the tubing assembly is flexible, and unassisted access to the straw is accordingly limited. Moreover, the fluid must be drawn through the tube and straw under suction provided by the user, an action which extremely weak users may not be capable of performing. In addition, cleaning of the tubing assembly is hindered by the fact that the assembly is semi-permanently mounted on the jug and its surrounding support structure, making it difficult or impossible to effectively flush the tubing assembly. This in turn tends to result in unsanitary operating conditions.

Another drinking device is disclosed in U.S. Pat. No. 5,057,077 to Turner et al. and includes a fluid filled bag, a mouthpiece, and a flexible tube supplying liquid from the bag to the mouthpiece and having a valve disposed therein for permitting the supply of fluid to the tube from the bag in discrete boluses. A nipple extends through the mouthpiece for access by the user, and the mouthpiece is designed for semipermanent positioning on the user's face with the nipple inserted in the user's mouth. Use of such a device would appear to result in significant discomfort to the user. Further, since the tube supplying fluid to the mouthpiece is flexible, the mouthpiece will fall to an inaccessible position should it become dislodged from the user's mouth, and thereby preclude access to the mouthpiece. In addition, the valve is specially designed to provide distinct boluses of fluid to the user of rather limited volume. This may prove frustrating to some users. Moreover, as with the Green patent discussed above, the tubing assembly is not easily cleaned and its extended use could result in unsanitary operating conditions.

OBJECTS AND SUMMARY OF THE INVENTION

It is therefore an object of the invention to provide a drinking device for incapacitated users which heightens the user's level of independence by permitting the semipermanent positioning of the nipple or valve of such a device at a location which is easily accessible by the mouth of the user.

Another object of the invention is to provide a drinking device of the type described above which is easily cleaned.

Yet another object of the invention is to provide a drinking device of the type described above which can assuredly and continuously supply fluid to the user upon demand with minimal effort by even the most incapacitated users.

In accordance with a first aspect of the invention, these and other objects are achieved by providing a drinking device comprising a source of liquid, a drinking valve, and a tubing assembly supplying liquid from the source to the valve. The tubing assembly includes a hollow flexible tube having an inlet connected to the source and an outlet connected to the valve, and a semi-rigid stiffener extending along and beside an outside edge of the flexible tube and being attached to the flexible tube, the stiffener being (a) sufficiently flexible to permit the tubing assembly to be bent into a position facilitating access to the valve by the mouth of a user and (b) sufficiently rigid to hold the tubing assembly in the position after bending.

The stiffener preferably includes a wire encased in a material forming the flexible tube, and even more preferably a stainless steel wire having a diameter of about 3/32 of an inch. Additional stiffening may be required for relatively long tubing assemblies, in which case a second wire may be provided and may be encased in the material and extending along and beside an outside edge of the flexible tube.

In order to facilitate use by even the most incapacitated users having little strength in their mouth or lungs, the valve preferably comprises a valve body, a valve element disposed in the body, a valve actuator which extends from the body and which, when deflected by the mouth of a user, opens the valve element, the valve element closing automatically upon release of the actuator. Preferably, the valve element comprises a diaphragm which is disposed in the body and which has apertures formed therethrough which are normally sealed against the body. The valve actuator in this instance comprises a valve stem extending longitudinally through the body and having a head which is seated against the diaphragm and a tail which, upon lateral deflection thereof by the user, shifts the head to deflect the diaphragm and unseal the apertures of the diaphragm from the body, thereby permitting fluid flow through the diaphragm. Means preferably extend outwardly from an outer periphery of the housing for permitting clamping by the mouth of the user onto the valve.

The source of liquid may be either unpressurized or pressurized. If unpressurized, the source preferably comprises a bottle having an upper inlet, a lower outlet, and an air hole formed in an upper surface thereof to prevent formation of a vacuum which could hinder e flow of fluid through the tubing assembly.

Another object of the invention is to provide an improved method of drinking for an incapacitated person.

In accordance with another aspect of the invention, this object is achieved by providing a method comprising positioning a tubing assembly for access by the mouth of an incapacitated user by bending a semi-rigid stiffener of the tubing assembly, attached to and extending along a flexible tube of the tubing assembly, so as to facilitate the positioning of a drinking valve disposed on an end of the tubing assembly proximate the mouth of the user, then actuating the valve using the mouth of the user, and then feeding liquid through the flexible tube and the valve and into the mouth of the user.

Yet another object of the invention is to provide a method of cleaning a drinking device for incapacitated persons.

In accordance with yet another aspect of the invention, this object is achieved by providing a method comprising removing a drinking valve from an outlet end of a tubing assembly supplying liquid from a source of liquid to the valve, the tubing assembly including a hollow, flexible tube and a semi-rigid stiffener extending along and beside an outside edge of the flexible tube and being attached to the flexible tube, the stiffener being (a) sufficiently flexible to permit the tubing assembly to be bent into a position facilitating access to the valve by the mouth of a user and (b) sufficiently rigid to hold the tubing assembly in the position after bending. Subsequent steps include detaching an outlet end of the tubing assembly from the source of liquid, and flushing the flexible tube without hindrance from any obstructions within the flexible tube, thereby cleaning the flexible tube.

These and other objects, features, and advantages of the invention will become apparent to those skilled in the art from the following detailed description and the accompanying drawings. It should be understood that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings in which like reference numerals represent like parts throughout, and in which.

DETAILED DESCRIPTION OF THE PREFERRED EMBODIMENTS

1. Resume

Pursuant to the invention, a drinking device is provided which is sanitary, easy to clean, and heightens the user's level of independence by (1) being readily yet semi-permanently locatable at a position permitting access to the device by the mouth of the user; and (2) being easily activated by the mouth of the user to reliably and continuously supply a potable liquid to the user upon demand using only the user's mouth. The device includes a mouth operated drinking valve the semi-permanent positioning of which for accessibility by the mouth of the user is made possible by a tubing assembly in the form a flexible tube supported by a stiffener. The stiffener permits the tubing assembly to be readily bent to position the tube and drinking valve as desired yet maintains its position after bending. The stiffener is provided on the outside rather than within the flexible tube to facilitate cleaning of the tube and thus to promote sanitary use. Cleaning is further facilitated and sanitary use further promoted through the use of an easily disassembled device including a bottle with a removable lid, an easily disassembled drinking valve, and easily detachable connection of the tubing assembly to the bottle and valve. A mounting bracket is also provided which detachably receives the bottle and which can be readily mounted on a wall or other support structure, an I.V. stand, or a wheelchair so as to assuredly provide the flow of fluid through the valve under gravity upon demand. Alternatively, the tubing assembly can be directly connected to a water pipe or another pressurized fluid source.

Figure 1:
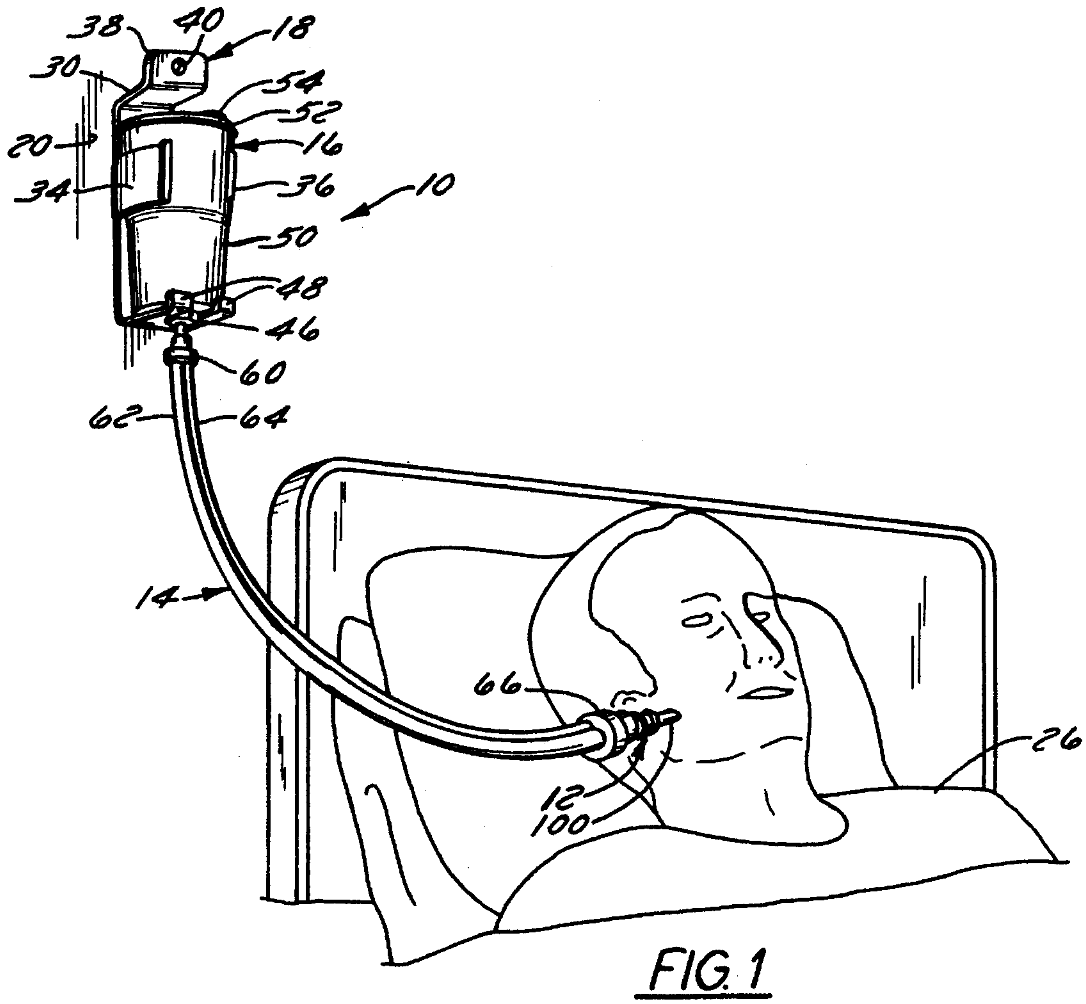
FIG. 1 is a perspective view illustrating a drinking device constructed in accordance with the present invention and mounted on a wall.
Figure 2:
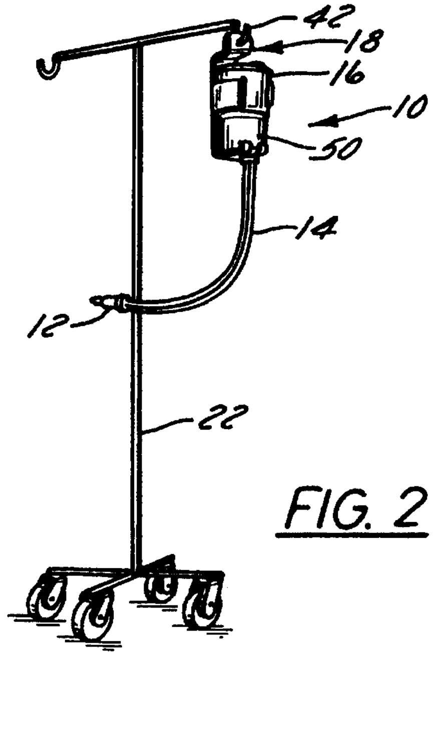
FIG. 2 illustrates the drinking device of FIG. 1 mounted on an intravenous or I.V. stand.
Figure 3:
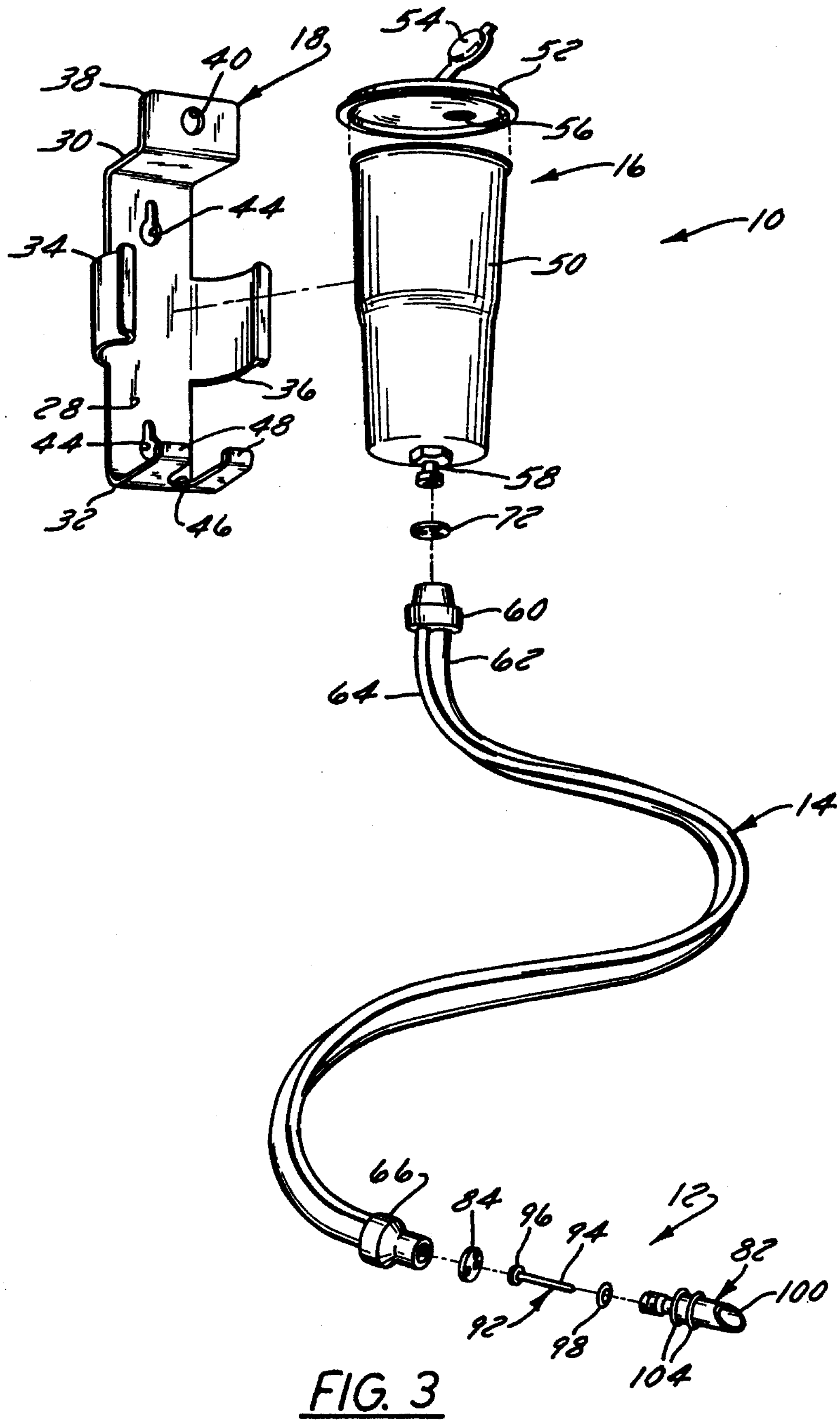
FIG. 3 is an exploded perspective view of the drinking device of FIGS. 1 and 2.
Figure 5:
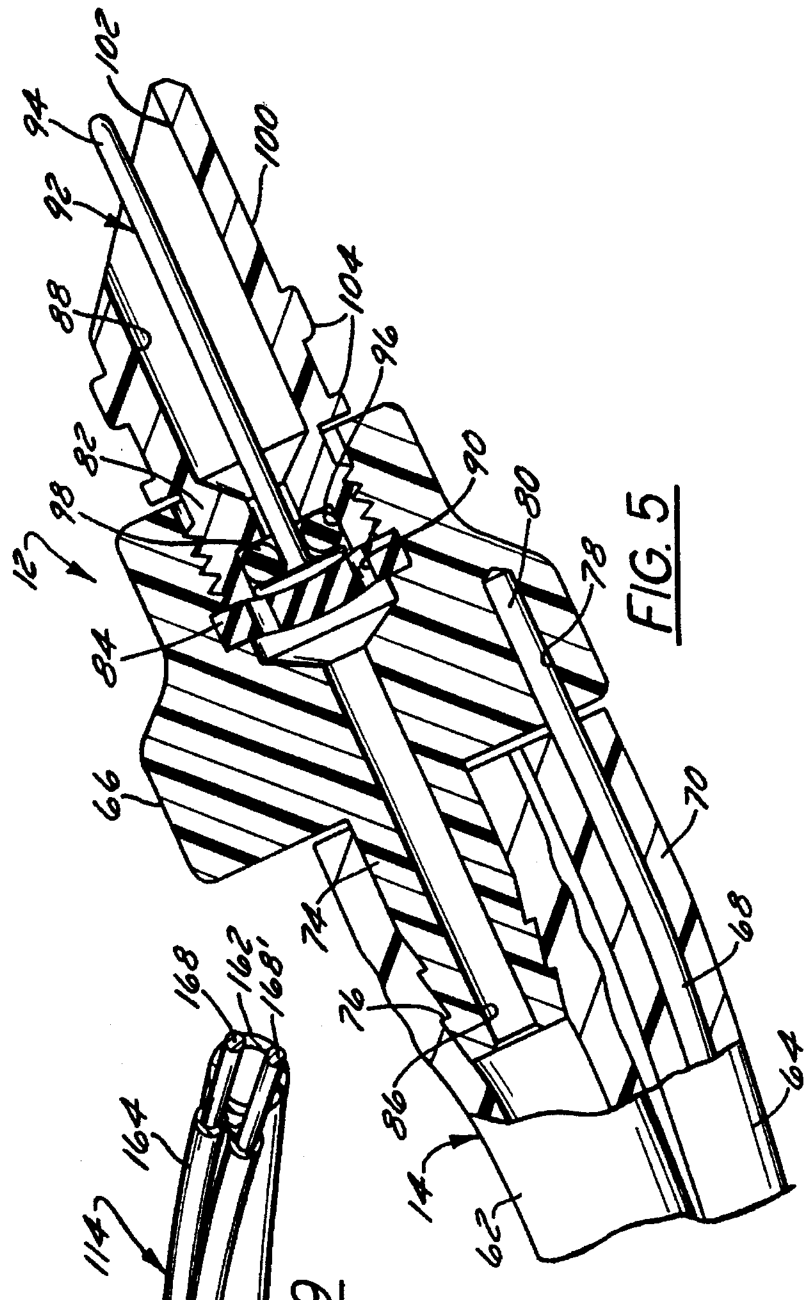
FIG. 5 is a partially cut-away elevation view of a drinking valve of the drinking device of FIGS. 1–3.
Figure 4:
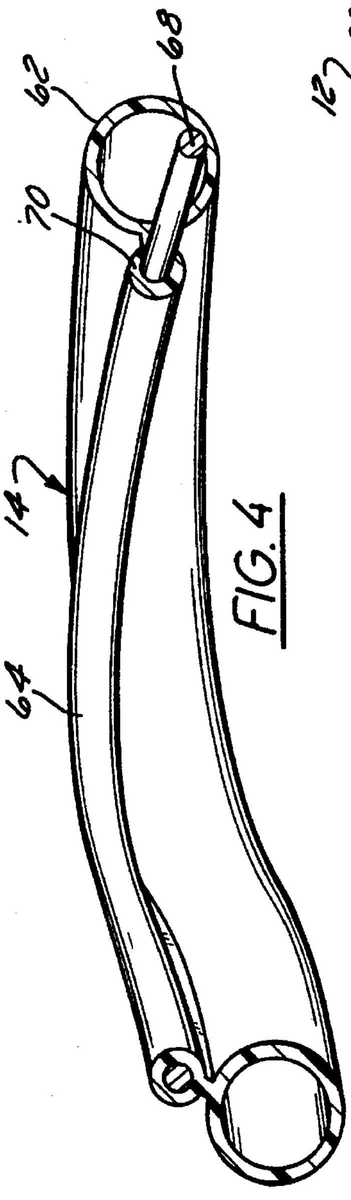
FIG. 4 is a perspective view of a portion of the tubing assembly of a drinking device of FIGS. 1–3.
Figure 6:
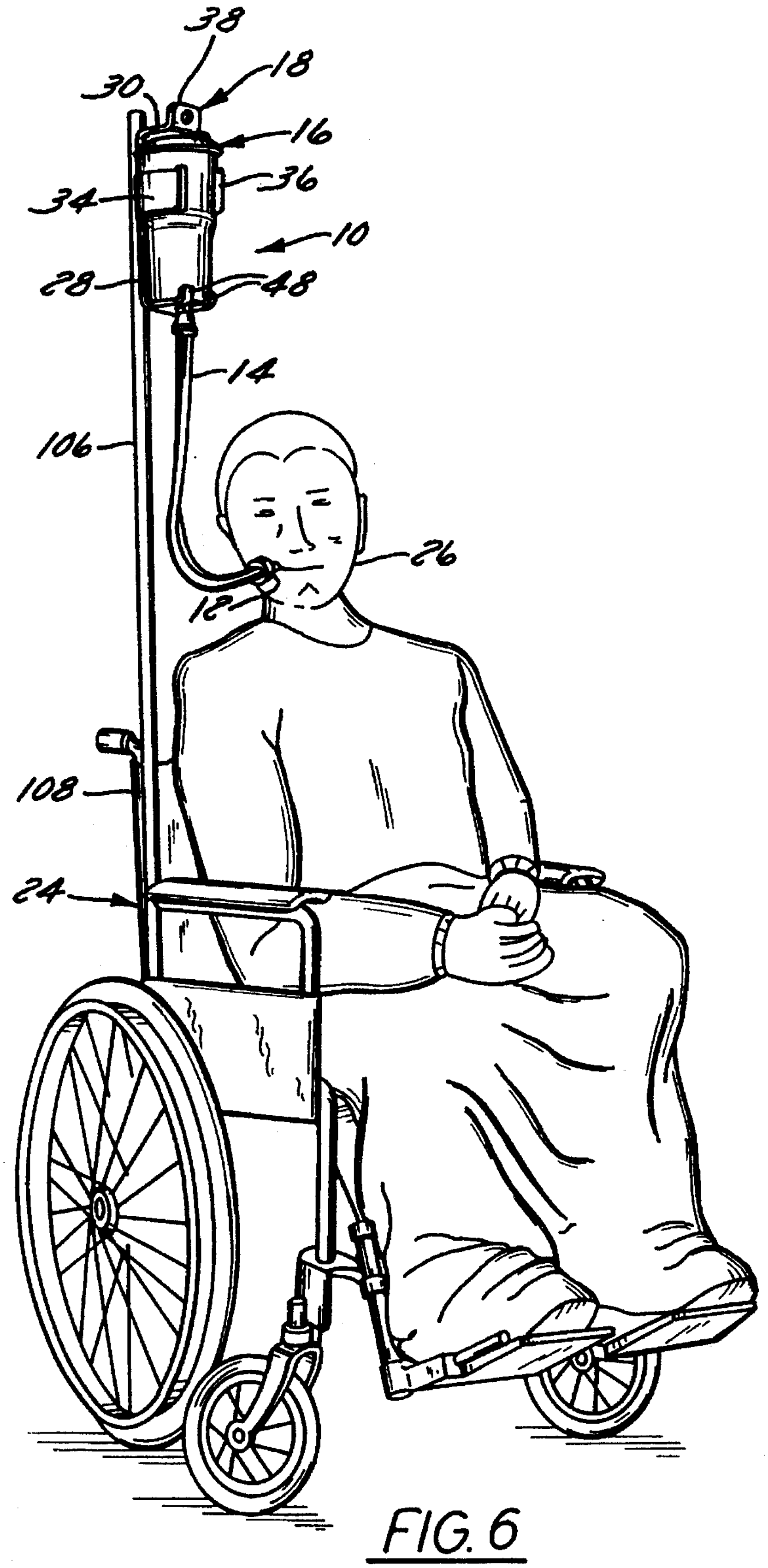
FIG. 6 is a perspective view illustrating the drinking device of FIGS. 1–3 mounted on a wheelchair.

2. Construction and Operation of Drinking Device Using a Nonpressurized Source of Fluid Referring now to FIGS. 1–6, a drinking device 10 includes a drinking valve 12, a tubing assembly 14, and a source of liquid 16. The source of liquid 16 may be any unpressurized or pressurized device capable of delivering fluid to the drinking valve through the tubing assembly and, in the embodiments illustrated in FIGS. 1–6, comprises a bottle supported on a mounting bracket 18. The mounting bracket 18 may be mounted on a wall 20 or the like as illustrated in FIG. 1, a portable or stationary I.V. stand 22 as illustrated in FIG. 2, a wheelchair 24 as illustrated in FIG. 6, or any other suitable support. The drinking device 10 of this embodiment is designed to supply water or another potable fluid by gravity to the mouth of a user 26 when the drinking valve 12 is actuated by the user's mouth.

The mounting bracket 18 is designed to be readily mounted on a suitable support and to releasably receive the bottle 16 without interference from the tubing assembly 14. To this end, the illustrated and preferred mounting bracket 18 includes a unitary metal member having a rear vertical backplate 28, a forwardly extending upper plate 30, a lower base 32, and a pair of side arms 34, 36. The upper plate 30 is bent upwardly at its front end to define a flange 38 having an aperture 40 formed therethrough for suspending the mounting bracket 18 and bottle 16 from a hook 42 of I.V. stand 22 or the like as illustrated in FIG. 2. Screw holes 44 (FIG. 3) or the like are formed through the backplate 28 for connecting the mounting bracket 18 to a wall 20 or similar support as illustrated in FIG. 1 or to another device as discussed below with respect to FIG. 6. The side arms 34, 36 are curved so as to generally correspond to the shape of the bottle 16 and present spring elements which expand when the bottle 16 is pushed into the bracket 18 and then snap onto the bottle 16 to relatively securely hold it in place. The base 32 has (1) a central slot 46 formed therethrough for receiving the end of the tubing assembly 14 and (2) outwardly extending tabs 48 at its front end for engaging the base of the bottle 16. Of course, the mounting bracket 18 need not be constructed as illustrated and described above but could comprise any structure capable of supporting the bottle 16 and of permitting cleaning of the bottle 16 and the tubing assembly 14. Mounting bracket 18 could also be eliminated altogether and the bottle 16 mounted on an existing support.

The bottle 16 may comprise any structure capable of storing liquid but is preferably designed to facilitate the flow of liquid to the tubing assembly 14 and also to facilitate drinking device disassembly and cleaning. To this end, the bottle 16 is formed from a cylindrical body 50 covered with a removable lid 52 having a cap 54 provided thereon which permits filling of the bottle 16 without removing the lid 52 and which also presents an air hole 56 which promotes the flow of liquid out of the bottle 16 by preventing a vacuum from forming. A connector extends from the body 50 and may comprise any suitable device for connection to the tubing assembly 14 and, in the illustrated embodiment, includes a male fitting 58 for cooperating with a female fitting 60 on the tubing assembly 14 as detailed below.

The tubing assembly 14 comprises an elongated hollow flexible tube 62 stiffened with a semirigid stiffener 64 and capped at its inlet end with the female fitting 60 and at its outlet end with a valve cap 66. The flexible tube 62 may be formed from flexible PVC, silicone rubber, or any flexible watertight material meeting FDA approval. The stiffener 64 may be any device which is sufficiently flexible to permit the tubing assembly 14 to be bent into a position facilitating access to the valve 12 by the mouth of the user 26 and yet sufficiently rigid to hold the tubing assembly 14 in this position after bending. A stainless steel wire 68 having a diameter of about 3/32" has been found to be particularly well suited for this purpose because it exhibits the required combination of flexibility and strength and yet is highly resistant to rust or corrosion.

The stiffener 64 is positioned outside rather than within the flexible tube 62 because it is important to minimize potential obstructions or other devices within the tube 62 which could hinder the flow of fluid through the tube 62 and/or hinder flushing of the tube 62 during cleaning or otherwise promote unsanitary operating conditions. The absence of any obstructions in the tube 62 may become particularly important if pulpy juices or sugar-based liquids are used which may tend to stick to stiffeners within the tube or to become lodged between such stiffeners and the wall of the tube. The wire 68 of stiffener 64 could thus be wrapped around the outside of the flexible tube 62 and/or taped or glued to the tube 62, but preferably is encased in the material 70 forming the flexible tube 62 so as to be formed integral therewith. This facilitates assembly, limits exposure of the wire 68 to the environment, and presents a clean, unitary appearance.

The female fitting 60 at the inlet end of the tubing assembly 14 and the valve cap 66 at the outlet end may comprise any suitable devices but preferably are designed to facilitate disassembling of the drinking device 10 and flushing of the flexible tube 62. To this end, the female fitting 60 receives the male fitting 58 with a conventional perforated diaphragm seal 72 therebetween which is removable to permit flushing and cleaning of the tubing assembly 14, and the valve cap 66 similarly receives a diaphragm 84 of the drinking valve 12 as detailed below.

The valve cap 66 may be connected to the tubing assembly 14 in any suitable manner. In the illustrated embodiment, the valve cap 66 has a shank 74 presenting barbs 76 (FIG. 5) which engage and grip the inner periphery of the flexible tube 62 and also has a bore 78 which receives an exposed end 80 of the wire 68. The female fitting 60 is attached to the inlet end of the tubing assembly 14 in the same manner.

Although the drinking valve 12 could take many forms, it is preferably constructed such that it (1) can be easily grasped and operated by the mouth of even the most incapacitated users, (2) continuously supplies liquid upon actuation at a rate which is comfortable to the user, (3) automatically returns to its closed state upon release, and (4) is easily disassembled for cleaning purposes. All of these characteristics are met by the illustrated valve 12, the internal construction and operation of which is identical to that disclosed in U.S. Pat. No. 3,550,560 to Edstrom, the disclosure of which is hereby incorporated by reference. The valve 12 includes a two-part body including (1) the valve cap 66, described above, and (2) a valve seat 82 threadedly connected to the valve cap 66 with a perforated diaphragm 84 clamped therebetween forming a valve element. Mating longitudinal bores 86, 88 extend through the valve cap 66 and the valve seat 82 and are separated by the diaphragm 84 such that the bore 86 in the valve cap 66 is sealed from the bore 88 in the valve seat 82 when the diaphragm 84 is in its undistorted flat condition in which the apertures 90 in the diaphragm 84 are sealed against an end face of the valve seat 82. A valve stem 92 serving as a valve actuator is disposed in the valve seat 82 and has a tail 94 extending through the bore 88 and a head 96 which is held against the lower face of the diaphragm 84 by a resilient rubber or synthetic rubber O-ring or D-ring 98. The tail 94 of the valve stem 92 extends into a beveled end portion defining a nipple 100 of the valve seat 82 and is accessible by the lips, teeth, or tongue of the user 26 so as to be easily deflectable into engagement with a peripheral wall 102 of the bore 88 and easily held in its deflected position. When in its deflected position, the tail 94 of the valve stem 92 shifts the head 96 to deflect the diaphragm 84 against the biasing forces of the diaphragm 84 and O-ring 98, thereby unsealing the apertures 90 in the diaphragm 84 from the valve seat 82 and permitting liquid flow through the diaphragm 84.

The outer surface of the valve seat 82 is designed to facilitate grasping of the valve 12 by the mouth of the user 26. To this end, a pair of circumferential rings 104 are formed on the outer surface of the valve seat 82 and permit grasping of the valve by the user's teeth or lips. It should be understood that these rings 104 are not essential to the operation of the valve 12 and could be replaced with radial lugs or other members permitting grasping, and could even be deleted altogether.

3. Use and Cleaning of Drinking Device Having Non-pressurized Fluid Source

To prepare the drinking device 10 for use, the mounting bracket 18 is positioned at a location permitting the flow of liquid from the bottle 16 to the user 26 by gravity and thus may be mounted on a wall 20 as illustrated in FIG. 1 or suspended from an I.V. stand 22 as illustrated in FIG. 2. The lid 52 of the bottle 16 is then removed, and the bottle 16 is filled with water or any other potable liquid. The lid 52 is then replaced, and the bottle 16 is mounted on the bracket 18 by inserting it laterally between the arms 34 and 36 and by sliding the end of the tubing assembly 14 through the slot 46 in the base 32 of the mounting bracket 18. Then, as illustrated in FIG. 1, the tubing assembly 14 is bent into a position facilitating access of the valve 12 by the mouth of the user 26 and is maintained in this position under the action of the stiffener 64. The user 26 then grasps the valve nipple 100 with his or her mouth and deflects the tail 94 of valve stem 92 with his or her teeth or lips. Liquid then flows through the valve 12 at a rate which is dependent upon the degree of deflection of the stem 92 and continues to flow at a constant rate as long as the user 26 desires. The stem 92 returns to its initial position upon release under the biasing forces of the diaphragm 84 and O-ring 98, thus automatically closing the valve 12 and terminating the flow of liquid therethrough. This prevents or at least inhibits fluids from wetting the bedding or clothes of the user 26 when he or she is finished drinking.

It can thus be seen that an attendant is required only to fill the bottle 16 and to initially position the tubing assembly 14 and thus the drinking valve 12 at a location which is accessible by the mouth of the user 26. The user 26 is then capable of obtaining fluids upon demand for extended periods of time (limited only by the capacity of the bottle 16) without further assistance from the attendant. This fosters considerable independence on the part of the user.

It is of course necessary to periodically clean the drinking device 10 to maintain sanitary operating conditions. Such cleaning is facilitated due to the fact that the drinking device 10 is easily disassembled and the fact that the flexible tube 62 of the tubing assembly 14 is easily flushed. Thus, the bottle 16 is simply removed from the bracket 18 and the lid 52 is removed to facilitate cleaning of the bottle 16. The tubing assembly 14 is disassembled simply by disconnecting the female fitting 60 on the inlet end from the male fitting 58 on the bottle 16 and removing the diaphragm 72. The valve 12 is similarly disassembled by unscrewing the valve seat 82 from the valve cap 66 and removing the diaphragm 84 (which removal, incidentally, can be performed by inserting the tail 94 of the valve stem 92 into an aperture 90 of the diaphragm 84 and thus does not require any special tooling). The flexible tube 62 can then be flushed with water or a cleaning solution or washed in a dishwasher without obstruction from any members within the flexible tube 62, thus promoting effective cleaning and sanitary operating conditions.

4. Construction and Operation of Modified Nonpressurized Drinking Devices

Referring now to FIG. 6, the drinking device 10 of FIGS. 1–5 can also be easily adapted for use on a wheelchair 24 by mounting the bracket 18 on a tube 106 by clamps (not shown) connected to the backplate 28 via screw holes 44. Tube 106 is in turn mounted on a frame 108 of the wheelchair 24 and is preferably adjustable, e.g., through telescoping upon loosening of a suitable fitting, so as to permit positioning of the bottle 16 at a preferred height above the head of the user. If the wheelchair 24 is provided with a reclining seat, the tube 106 should be mounted on the frame 108 of the seat so as to recline with the seat and thus assure the desired spacing between the user 26 and the drinking device 10 at all times.

Figure 9:
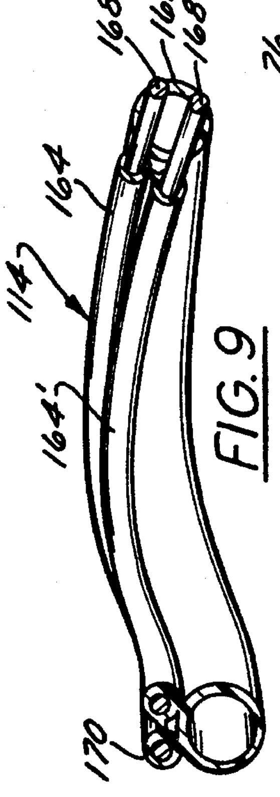
FIG. 9 is a perspective view of a portion of a second type of tubing assembly usable with the drinking devices of FIGS. 1–8.

While the tubing assembly 14 of the drinking device 10 as described above employs only a single stiffener 64, other stiffeners may be desired, particularly for relatively long tubing assemblies. The number of stiffeners employed and the thickness of each wire stiffener will, of course, depend upon the desired rigidity of the tubing assembly. Thus, referring to FIG. 9, a tubing assembly 114 is illustrated which has a second stiffener 164' provided adjacent a first stiffener 164 and formed from a stainless steel wire 168'. Stainless steel wire 168' is encased by a material 170 which forms flexible tube 162 and which is the same material that encases the wire 168 of the first stiffener 164. Tubing assembly 114 is otherwise identical in construction and operation to the assembly 14 described above, and corresponding elements are designated by the same reference characters, incremented by 100.

Figure 7:
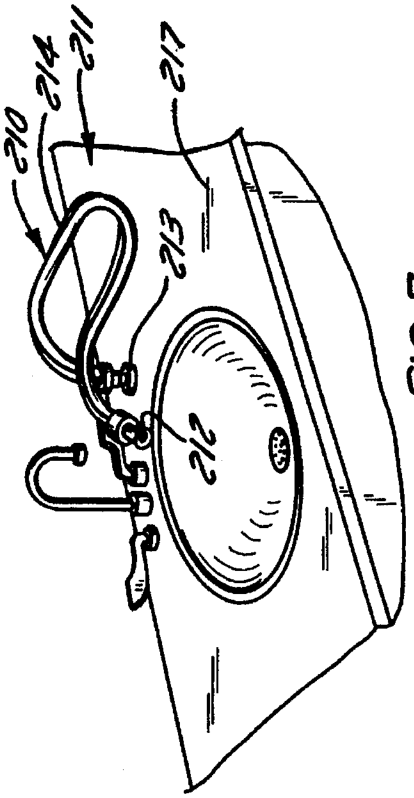
FIGS. 7 and 8 are a perspective and side elevation view, respectively, of a drinking device constructed in accordance with a second embodiment of the invention and connected to a pressurized fluid source.
Figure 8:
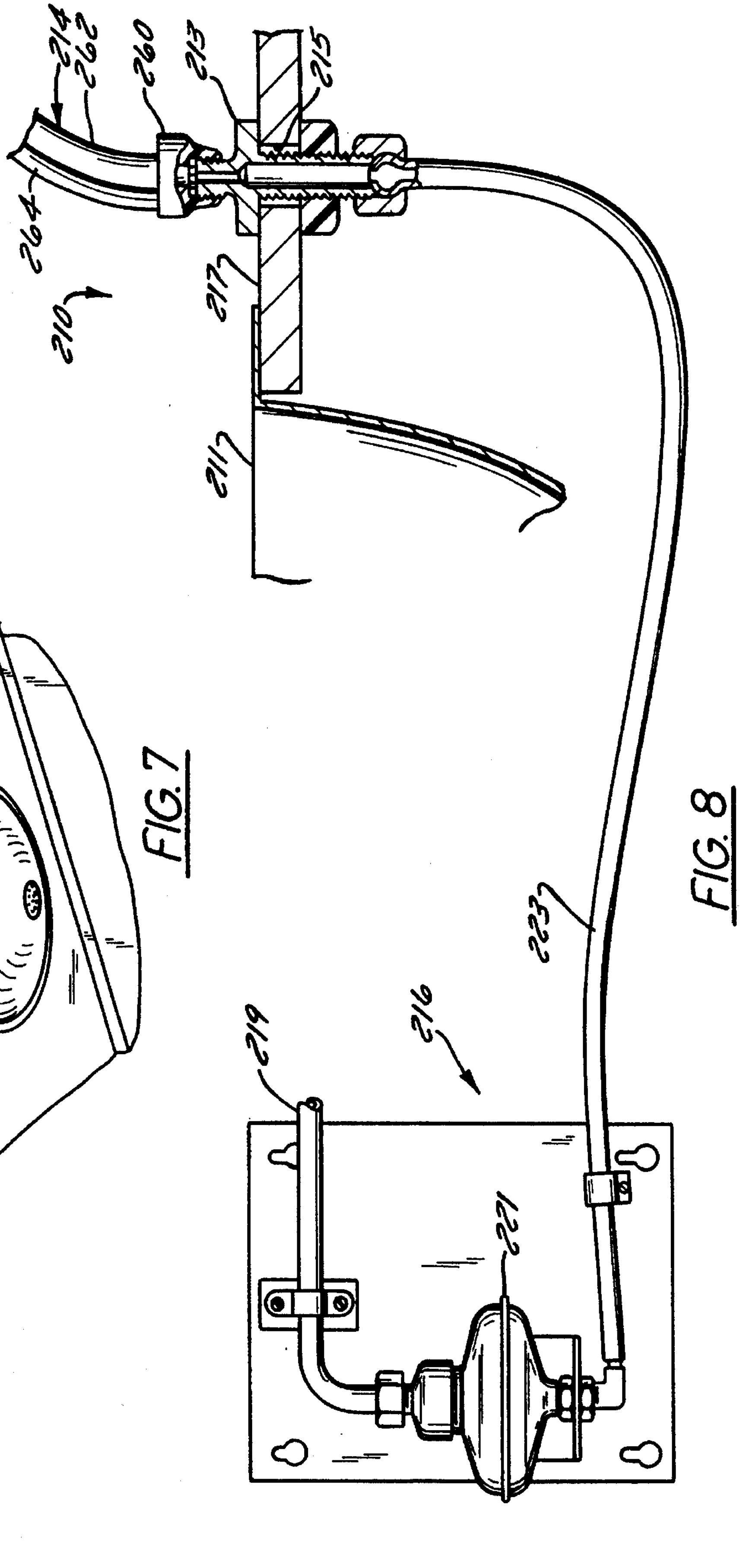

5. Construction and Operation of Pressurized Drinking Device and Other Alternative Structures The drinking devices as described above all employ as a fluid source a nonpressurized bottle. A pressurized source could, however, be employed to obviate the need for gravity feed and to provide a fluid source of essentially limitless capacity. Thus, referring to FIGS. 7 and 8, a drinking device 210 is provided which includes a pressurized fluid source 216. Device 210 is mounted directly on a bathroom vanity 211 or the like with a female fitting 260 on an inlet end of a tubing assembly 214 thereof being connected to an outlet end of a bulkhead fitting 213 mounted in an aperture 215 formed in a counter 217 of vanity 211. The fluid source 216 includes an existing water line 219, a pressure reducing valve 221, and a low pressure feed line 223. Feed line 223 is connected at its outlet to the bulkhead fitting 213 and its inlet to the pressure reducing valve 221. The pressure reducing valve 221 in turn has an outlet connected to the feed line 223 and an inlet connected to the water line 219. The drinking device 210 as thus constructed is otherwise identical to that described above in connection with FIGS. 1–6, and its elements are denoted by the same reference characters, incremented by 200. The tubing assembly 214 can thus be bent to and maintained in a position in which the drinking valve 212 is easily accessible by the mouth of a user from a wheelchair positioned adjacent the vanity 211.

It should be understood that many changes and modifications could be made to the invention without departing from the spirit thereof. For instance, the pressurized fluid source illustrated in FIGS. 7 and 8 could be replaced by a permanently pressurized or pump pressurized container which would have the mobility advantages of the embodiment of FIGS. 1–6 but which would not have to be positioned at a location above the head of the user. Moreover, an unpressurized container, if employed, could take the form of a collapsible bag or some other device not requiring the breather hole provided on the rigid bottle disclosed above. Other changes and modifications falling within the scope of the invention will become apparent from a reading of the appended claims.

I claim:

1. A drinking device comprising:

(A) a source of liquid;

(B) a drinking valve; and (C) a tubing assembly for supplying liquid from said source to said valve, said tubing assembly including (1) a hollow, flexible tube having an inlet connected to said source and an outlet connected to said valve, and (2) a semi-rigid stiffener extending along and beside an outside edge of said flexible tube and being attached to said flexible tube, said stiffener, in combination with said flexible tube, being (a) sufficiently flexible to permit said tubing assembly to be semi-permanently bent into a position in which said valve is easily accessible by the mouth of a user and (b) sufficiently rigid to hold said tubing assembly in said position after bending while forming the sole support for said valve.

2. A drinking device as defined in claim 1, wherein said stiffener comprises a wire encased in a material forming said flexible tube.

3. A drinking device as defined in claim 2, wherein said wire is composed of stainless steel and has a diameter of about 3/32 of an inch.

4. A drinking device as defined in claim 1, wherein said valve comprises (A) a valve body;

(B) a valve element disposed in said body; and (C) a valve stem which extends longitudinally from said body and which, when deflected laterally by the mouth of the user, distorts and opens said valve element, said valve element closing automatically upon release of said valve stem.

5. A drinking device comprising:

(A) a source of liquid;

(B) a drinking valve; and (C) a tubing assembly fog supplying liquid from said source to said valve, said tubing assembly including (1) a hollow, flexible tube having an inlet connected to said source and an outlet connected to said valve, and (2) a semi-rigid stiffener extending along and beside an outside edge of said flexible tube and being attached to said flexible tube, said stiffener being (a) sufficiently flexible to permit said tubing assembly to be bent into a position facilitating access to said valve by the mouth of a user and (b) sufficiently rigid to hold said tubing assembly in said position after bending; wherein said valve comprises a valve body, a valve element disposed in said body, and a valve actuator which extends from said body and which when deflected by the mouth of the user, opens said valve element, said valve element closing automatically upon release of said actuator, wherein said valve element comprises a diaphragm which is disposed in said body and which has apertures formed therethrough which are normally sealed against said body, and wherein said valve actuator comprises a valve stem extending longitudinally through said body and having a head which is seated against said diaphragm and a tail which, upon lateral deflection thereof by the user, shifts said head to deflect said diaphragm and unseal said apertures of said diaphragm from said body, thereby permitting fluid flow through said diaphragm.

6. A drinking device as defined in claim 5, wherein said valve body has a beveled lower end having said tail of said valve stem extending at least partially therethrough so as to be accessible by the user.

7. A drinking device as defined in claim 4, further comprising means, extending outwardly from an outer periphery of said body, for permitting clamping by the mouth of the user onto the valve.

8. A drinking device as defined in claim 1, wherein said source comprises a bottle having an upper inlet, a lower outlet, and an air hole formed in an upper surface thereof.

9. A drinking device comprising:

(A) a bottle having an upper inlet and a lower outlet;

(B) a drinking valve;

(C) a tubing assembly for supplying liquid from said bottle to said valve, said tubing assembly including (1) a hollow, flexible tube having an inlet connected to said source and an outlet connected to said valve, and (2) a semi-rigid stiffener extending along and beside an outside edge of said flexible tube and being attached to said flexible tube, said stiffener being (a) sufficiently flexible to permit said tubing assembly to be bent into position facilitating access to said valve by the mouth of a user (b) sufficiently rigid to hold said tubing assembly in said position after bending; and (D) a mounting bracket which supports said bottle, said mounting bracket including (1 ) a base having an aperture formed therethrough for the passage of said tubing assembly; and (2 ) arms for engaging a side surface of said bottle.

10. A drinking device as defined in claim 1, further comprising a first connecter on said source, a second, mating connecter on said inlet of said tubing assembly, and a perforated diaphragm disposed in said second connecter.

11. A drinking apparatus comprising:

(A) a source of liquid;

(B) a drinking valve; and (c) a tubing assembly for supplying liquid from said source to said valve, said tubing assembly including (1) a hollow, flexible tube having an inlet connected to said source and an outlet connected to said valve, and (2) a semi-rigid stiffener comprising a wire extending along and beside an outside edge of said flexible tube and being encased by a material forming said flexible tube, said stiffener, in combination with said flexible tube, being (a) sufficiently flexible to permit said tubing assembly to be semi-permanently bent into a position in which said valve is easily accessible by the mouth of a user and (b) sufficiently rigid to hold said tubing assembly in said position after bending while forming the sole support for said valve.

12. A drinking apparatus comprising:

(A) a source of liquid;

(B) a drinking valve including (1) a valve body, (2) a diaphragm which is disposed in said body and which has apertures formed therethrough which are normally sealed against said body, and (3) a valve stem extending longitudinally through said body and having a head which is seated against said diaphragm and a tail which upon lateral deflection thereof by the user, shifts said head to deflect said diaphragm and unseal said apertures of said diaphragm from said body, thereby permitting fluid flow through said diaphragm; and (C) a tubing assembly for supplying liquid from said source to said valve, said tubing assembly including (1) a hollow flexible tube having an inlet connected to said source and an outlet connected to said valve, and (2) a semi-rigid stiffener comprising a wire extending along and beside an outside edge of said flexible tube and being encased by a material forming said flexible tube, said stiffener being (a) sufficiently flexible to permit said tubing assembly to be bent into a position facilitating access to said valve by the mouth of a user and (b) sufficiently rigid to hold said tubing assembly in said position after bending.

13. A drinking apparatus comprising:

(A) a bottle having an upper inlet, a lower outlet, and an air hole formed in an upper surface thereof;

(B) a drinking valve including (1) a valve body;

(2) a diaphragm which is disposed in said body and which has apertures formed therethrough which are normally sealed against said valve body, and (3) a valve stem extending longitudinally through said body and having a head which is seated against said diaphragm and a tail which upon lateral deflection thereof by a user, shifts said head to deflect said diaphragm and unseal said apertures of said diaphragm from said valve body, thereby permitting fluid flow through said diaphragm;

(C) a tubing assembly for supplying liquid from said bottle to said valve, said tubing assembly including (1) a hollow, flexible tube having an inlet connected to said outlet of said bottle and an outlet connected to said valve, and (2) a semi-rigid stiffener comprising a wire extending along and beside an outside edge of said flexible tube and being encased by a material forming said flexible tube, said stiffener being (a) sufficiently flexible to permit said tubing assembly to be bent into a position facilitating access to said valve by the mouth of the user and (b) sufficiently rigid to hold said tubing assembly in said position after bending; and (D) a mounting bracket which supports said bottle, said mounting bracket including (1) a base having an aperture formed therethrough for the passage of said tubing assembly, and (2) arms for engaging a side surface of said bottle.

14. A method comprising:

(A) positioning a tubing assembly for access by the mouth of an incapacitated user by semi-permanently bending a semi-rigid stiffener of said tubing assembly, attached to and extending along a flexible tube of said tubing assembly, so as to position a drinking valve disposed on an end of said tubing assembly in an accessible position proximate the mouth of the user;

(B) maintaining said valve in said accessible position using only said tubing assembly;

(C) actuating said valve using the mouth of the user; and (D) feeding liquid through said flexible tube and said valve and into the mouth of the user.

15. A method as defined in claim 14, wherein said actuating step comprises laterally deflecting a stem of said valve using the mouth of the user.

* * * * *